(12) United States Patent
Ho et al.

(10) Patent No.: US 10,686,096 B2
(45) Date of Patent: *Jun. 16, 2020

(54) OPTICAL SENSOR MODULE AND A WEARABLE DEVICE INCLUDING THE SAME

(71) Applicants: LITE-ON OPTO TECHNOLOGY (CHANGZHOU) CO., LTD., Jiangsu Province (CN); LITE-ON TECHNOLOGY CORP., Taipei (TW)

(72) Inventors: Tsan-Yu Ho, Taipei (TW); Chen-Hsiu Lin, Taipei (TW); Meng-Sung Chou, Taipei (TW)

(73) Assignees: LITE-ON OPTO TECHNOLOGY (CHANGZHOU) CO., LTD., Jiangsu Province (CN); LITE-ON TECHNOLOGY CORP., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,182

(22) Filed: Nov. 12, 2018

(65) Prior Publication Data

US 2019/0081196 A1 Mar. 14, 2019

Related U.S. Application Data

(63) Continuation of application No. 15/789,181, filed on Oct. 20, 2017, now Pat. No. 10,134,939.

(30) Foreign Application Priority Data

Oct. 24, 2016 (CN) .......................... 2016 1 0939481

(51) Int. Cl.
*H01L 31/14* (2006.01)
*A61B 5/026* (2006.01)
*H01L 31/173* (2006.01)
*H01L 31/02* (2006.01)
*H01L 31/024* (2014.01)
(Continued)

(52) U.S. Cl.
CPC .......... *H01L 31/143* (2013.01); *A61B 5/0261* (2013.01); *H01L 31/024* (2013.01); *H01L 31/02005* (2013.01); *H01L 31/173* (2013.01); *A61B 5/14552* (2013.01); *A61B 5/681* (2013.01); *A61B 5/6831* (2013.01); *A61B 2562/0233* (2013.01); *A61B 2562/166* (2013.01); *H01L 2224/48091* (2013.01); *H01L 2224/73265* (2013.01)

(58) Field of Classification Search
CPC ............................................. H01L 2224/48091
See application file for complete search history.

(56) References Cited

U.S. PATENT DOCUMENTS

| 10,134,939 B2 * | 11/2018 | Ho ..................... H01L 31/02005 |
| 2007/0126915 A1 * | 6/2007 | Webster ............... H04N 5/2253 348/340 |

(Continued)

*Primary Examiner* — Thao P Le
(74) *Attorney, Agent, or Firm* — Rosenberg, Klein & Lee

(57) ABSTRACT

A lead frame includes a main plate and a side plate. The main plate has a support portion and a projecting portion. The support portion has two opposite first sides and a support face located between the first sides. The projecting portion projects upward from one of the first sides in a direction opposite to the support face. The side plate is disposed separately from the one of the first sides of the support portion and is spaced apart from the projecting portion.

20 Claims, 16 Drawing Sheets

(51) Int. Cl.
   *A61B 5/1455*  (2006.01)
   *A61B 5/00*    (2006.01)

(56) References Cited

U.S. PATENT DOCUMENTS

| | | | |
|---|---|---|---|
| 2007/0126916 A1* | 6/2007 | Webster | H04N 5/2253 |
| | | | 348/340 |
| 2012/0051017 A1* | 3/2012 | Lee | H05K 1/182 |
| | | | 361/761 |
| 2012/0313264 A1* | 12/2012 | Sato | H01L 23/13 |
| | | | 257/783 |
| 2015/0293625 A1* | 10/2015 | Narayanasamy | H03K 17/962 |
| | | | 345/174 |

* cited by examiner

OPTICAL SENSOR MODULE AND A WEARABLE DEVICE INCLUDING THE SAME

CROSS-REFERENCE TO RELATED APPLICATION

This application is a continuation application of U.S. patent application Ser. No. 15/789,181, filed on Oct. 20, 2017, which claims priority to Chinese Patent Application No. 201610939481.1, filed on Oct. 24, 2016.

FIELD

The disclosure relates to a sensor module and a wearable device including the sensor module, and more particularly to an optical sensor module and a wearable device including the optical sensor module.

BACKGROUND

As shown in FIG. 1, a conventional optical sensor module 1 for the use of photoplethysmography (PPG) includes a printed circuit board 11 (PCB) having opposite first and second faces 111, 112, a light-receiver 12 disposed on the first face 111, two light-emitters 13 disposed on the first face 111 and located respectively at two opposite sides of the light-receiver 12, and a light-blocking wall 14 disposed on the first face 111. The light-blocking wall 14 surrounds the light-receiver 12 and the light-emitters 13 and separates the light-receiver 12 from the light-emitters 13. When the optical sensor module 1 is used to make physiological measurement, the light-emitters 13 emit light to irradiate a biological body, and the light-receiver 12 receives the light reflected from or transmitting through the biological body and produces an optical signal representative of a physiological status of the biological body.

Due to material properties or structural thickness of the light-blocking wall 14, the light-blocking wall 14 may be unable to effectively block the light emitted from the light-emitters 13, and the light leaking from the light-blocking wall 14 may interfere with the light received by the light-receiver 12. In addition, because the PCB 11 has poor heat dissipation, temperature deviation in the optical sensor module 1 may affect the results of measurement.

SUMMARY

Therefore, an object of the present disclosure is to provide a lead frame for an optical sensor module.

Accordingly, a lead frame includes a main plate and at least one side plate. The main plate has a support portion and at least one projecting portion. The support portion has two opposite first sides and a support face located between the first sides. The at least one projecting portion projects upward from one of the first sides in a direction opposite to the support face. The at least one side plate is disposed separately from the one of the first sides of the support portion and is spaced apart from the at least one projecting portion.

Another object of the present disclosure is to provide an optical sensor module that can prevent light leakage and improve heat dissipation.

Accordingly, an optical sensor module includes a lead frame as described above, a receiver unit, at least one light-emitting unit and a housing. The receiver unit includes a light receiver that is disposed on the support face and that has a light receiving face opposite to the support face. The at least one light-emitting unit includes a light-emitter that is disposed on a mounting face of the at least one side plate and that has a light-emitting face opposite to the mounting face. The housing is molded over the lead frame.

Still another object of the present disclosure is to provide a wearable device for being worn by a user with skin contact to record photoplethysmogram signals.

Accordingly, a wearable device includes a casing, a printed circuit board, and an optical sensor module as described above. The casing includes a casing body and a wearing member connected to the casing body to be worn by a user. The casing body has a cover for contacting the user's skin. The printed circuit board is disposed in the casing body. The optical sensor module is electrically connected to the printed circuit board and is located between the cover and the printed circuit board.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
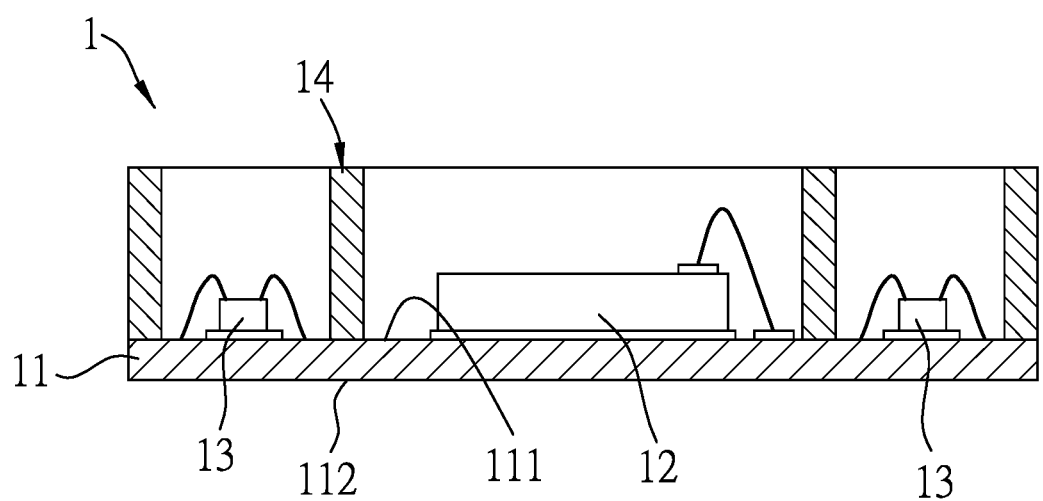
FIG. 1 is a sectional view of a conventional optical sensor module.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 2 to 7, an optical sensor module (O) according to a first embodiment of the present disclosure includes a lead frame (L), a receiver unit 4, at least one light-emitting unit 5 and a housing formed between the receiver unit 4 and the light-emitting unit 5 at least.

The lead frame (L) includes a main plate 2 and at least one side plate 3. The main plate 2 has a support portion 21, at least one projecting portion 22, a first leg portion 23 and a second leg portion 24. The support portion 21 has two opposite first sides 211, two opposite second sides 212 each of which is interconnected between the two opposite first sides 211, a support face 213 surrounded by the two opposite first sides 211 and the two opposite second sides 212, and a back face 214 disposed below the support face 213. In this embodiment, there are two projecting portions 22 which respectively project upward from the opposite first sides 211 of the support portion 21 in a direction opposite to the support face 213. The first leg portion 23 is disposed on one of the two opposite second sides 212 in a spaced-apart manner. The second leg portion 24 is connected to another one of the two opposite second sides 212. The first and second leg portions 23, 24 extend away from each other with respect to the support portion 21. In addition, each of the first and second leg portions 23, 24 has a bottom end coplanar with the back face 214.

In this embodiment, the at least one side plate (3) includes two side plates 3 are spaced apart from each other, are respectively proximal to and spaced apart from the opposite first sides 211 of the supporting portion 21, and are respectively spaced apart from the projecting portions 22. Each of the side plates 3 has a mount portion 31, a third leg portion 32 and a fourth leg portion 33. The mount portion 31 has the mounting face 311. The third leg portion 32 is spaced apart from the mount portion 31 and disposed at the same side as that of the first leg portion 23. The fourth leg portion 33 is connected to the mount portion 31 and disposed at the same side as that of the second leg portion 24. In order to connect a printed circuit board (not shown), the bottom ends of the first and second leg portions 23, 24 of the main plate 2 and the bottom ends of the third and fourth leg portions 32, 33 of the side plates 3 are coplanar with each other. In addition, the lead frame (L) is made from, but is not limited to, a same metal material. Specially, the lead frame (L) is made from a ductile metal material, such as a copper.

Figure 2:
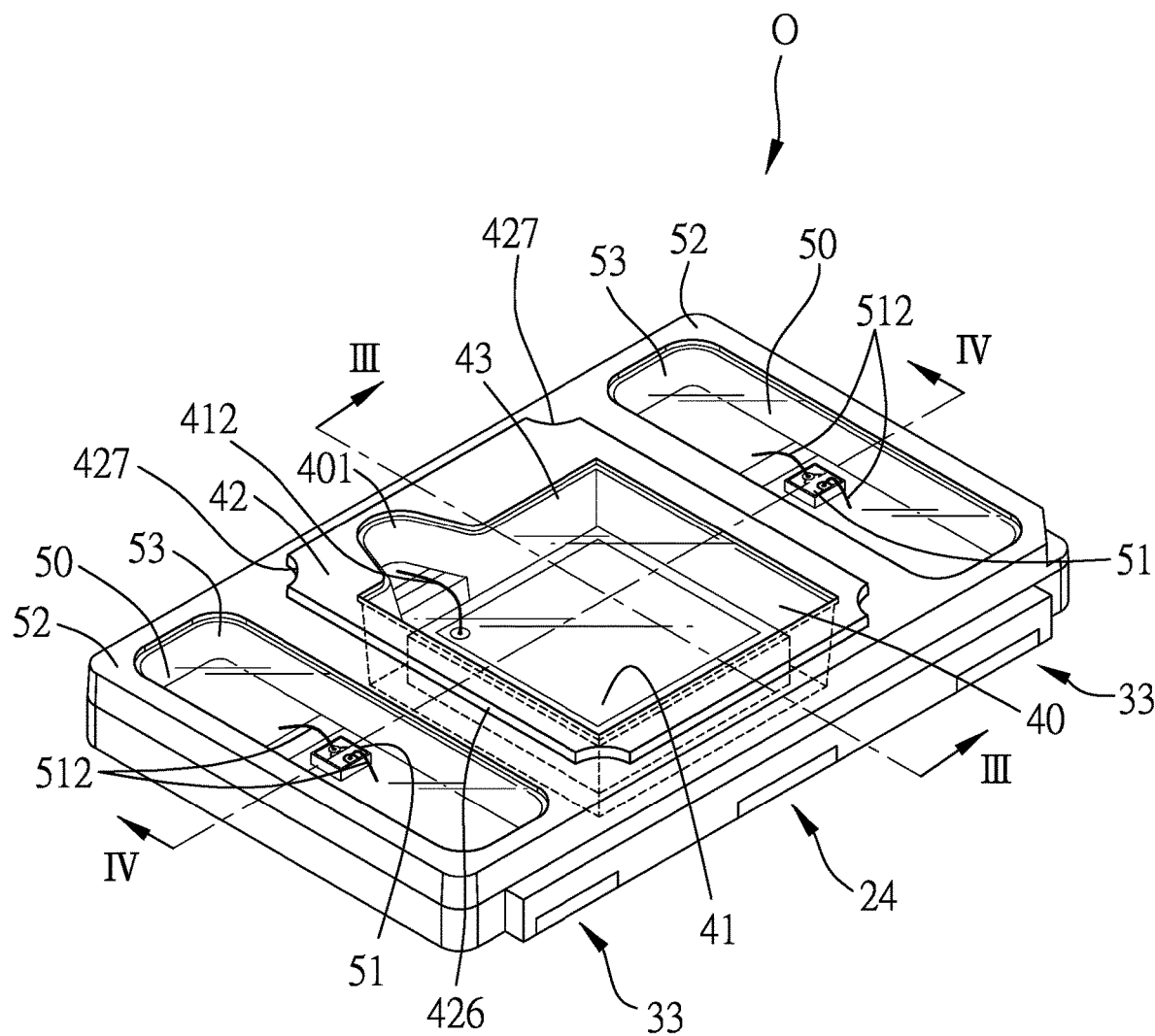
FIG. 2 is an optical sensor module of a first embodiment according to the present disclosure.
Figure 3:
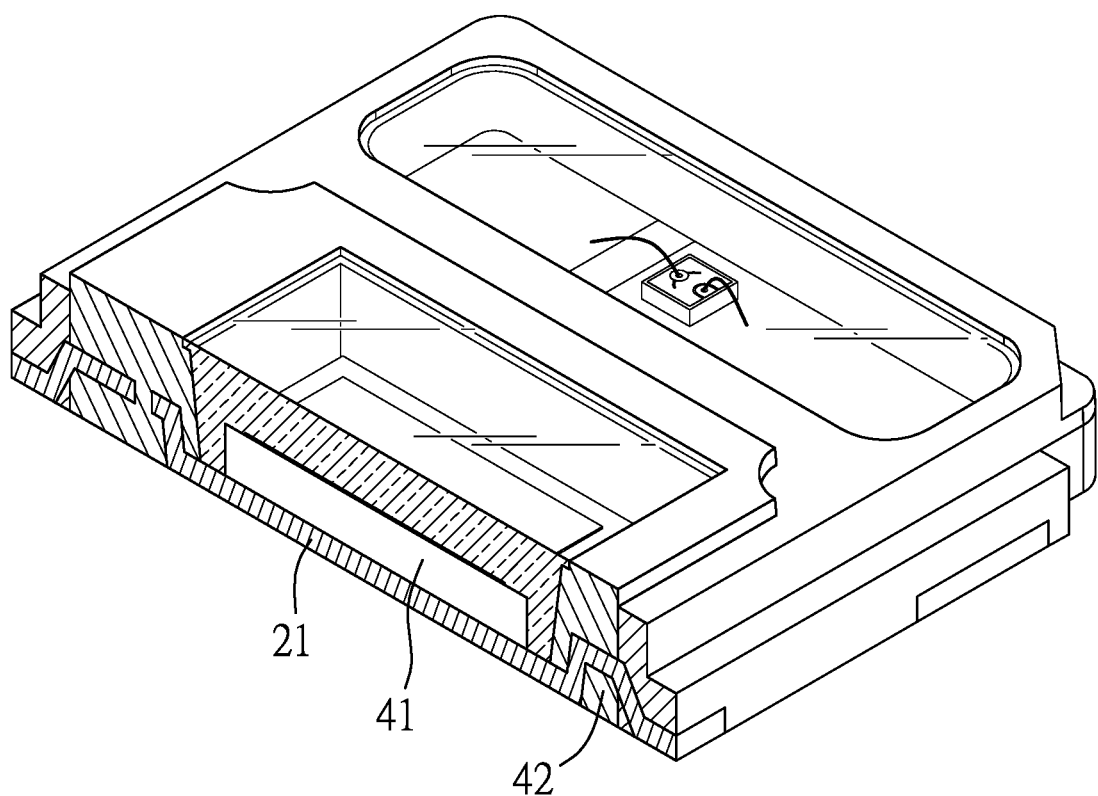
FIG. 3 is a partly sectioned view taken along line III-III of FIG. 2.
Figure 4:
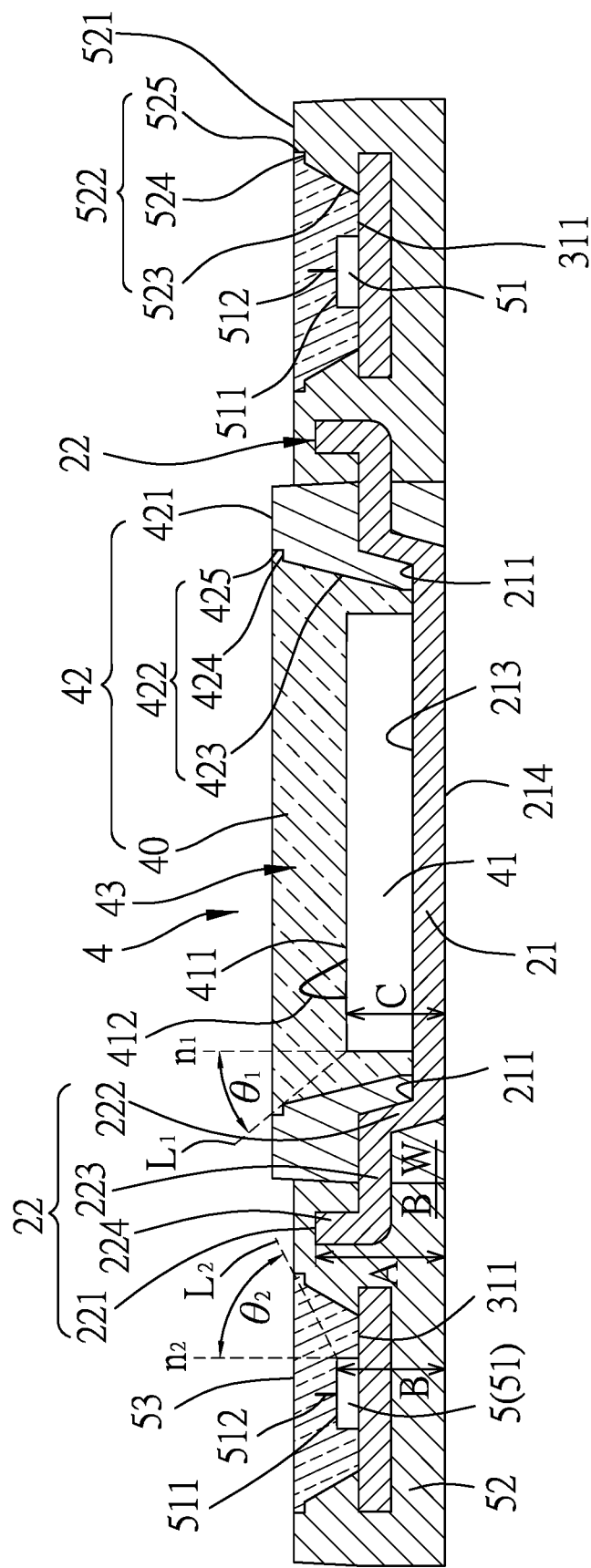
FIG. 4 is a sectioned view taken along line IV-IV of FIG. 2.

As shown in FIGS. 2 to 4, the receiver unit 4 includes a light receiver 41 and a first light-transmissible encapsulant 43. The light receiver 41 is disposed on the support face 213 and has a light receiving face 411 opposite to the support face 213. The light-transmissible encapsulant 43 encapsulates the light receiver 41 and covers the support face 213. In this embodiment, the light receiver 41 is a photo-plethysmogram (PPG) detector to receive and detect PPG signals.

Each of the light-emitting units 5 includes a light-emitter 51 and a second light-transmissible encapsulant 53. The light-emitters 51 of the light-emitting units 5 are respectively disposed on the mounting faces 311 of the side plates 3. The light-emitter 51 of each of the lighting units 5 has a light-emitting face 511 opposite to the mounting face 311 of a respective one of the side plates 3. The second light-transmissible encapsulant 53 encapsulates the light-emitter 51 and covers the mounting face 311 of the respective side plates 3. The first and second light-transmissible encapsulants 43, 53 can be made from a light-transmissible material, such as an epoxy resin material, an acrylic resin material, a silicon material, etc.

The housing is molded over the lead frame (L), and includes a first light-blocking wall 42 and a second light-blocking wall 52.

The first light-blocking wall 42 is molded over the main plate 2 and has a first opening 40 exposing the first light-transmissible encapsulant 43 and the light-receiver 41. As shown in FIG. 3, the light-receiver 41 is spaced apart from and surrounded by the first light-blocking wall 42. As shown in FIG. 2, the first opening 40 is square, and the first light-blocking wall 42 further has a sub-opening 401 extending from the opening 40 toward the first leg portion 23. As such, the first leg portion 23 is exposed from the sub-opening 401, and the light-receiver 41 is allowed to be electrically connected to the first leg portion 23 through the sub-opening 401.

The second light-blocking wall 52 is molded over the two side plates 3, extends around the first light-blocking wall 42, and includes two second openings 50 that are respectively disposed on two opposite sides of the first opening 40 and that respectively expose the light-emitting units 5. The first and second light-blocking walls 42, 52 adjoin each other between the first and second openings 40, 50 to form two common light barrier walls (see FIG. 4). As shown in FIG. 4, each of the projecting portions 22 is disposed between the first opening 40 and one of the second openings 50, and is completely enclosed by one of the common light barrier walls (BW). Alternatively, each projecting portions 22 may be partially enclosed by the common light barrier wall (BW).

Referring back to FIGS. 2, 4 to 7, each of the projecting portions 22 of the main plate 2 has a top face 221, an inclined section 222, a connection section 223 and a light partition section 224. The top face 221 extends away from the support face 213 of the support portion 21. The inclined section 222 adjoins a respective one of the two opposite first sides 211 and inclines the support face 213 by an obtuse angle. The connection section 223 extends horizontally from the inclined section 222 toward the mounting face 311 of the respective side plate 3. The light partition section 224 extends upwardly from the connection section 223 in a direction away from the support face 213. In addition, the light-receiving face 411 is lower than the light-emitting face 511. The light partition section 224 has the top face 221 higher than the light receiving face 411 and the light emitting face 511. That is to say, height (A) is higher than height (B) and height (C) in FIG. 4. The support portion 21 is a downset compared to the side plates 3. As such, the height (C) of the light-receiving face 411 in the optical sensor module (O) can be effectively lowered. Accordingly, the height (A) of the top face 221 of the projecting portion 22 can be reduced for slimming the optical sensor module (O). By virtue of the arrangement that the top face 221 of the projecting portion 22 is not lower than the light receiving face 411 (i.e., A≥C, preferably A>C in FIG. 4), the projecting portion 22 is proximal to the light emitter 51, the support portion 21 is a downset, and the top face 221 of the projecting portion 22 is not lower than the light emitting face 511 (i.e., A≥B, preferably A>B in FIG. 4), the light receiver 41 is prevented from receiving the light directly emitted from the light emitters 51, thereby enhancing the signal-to-noise (SNR) ratio of the optical sensor module (O). In addition, the back face 214 of the support portion 21 is exposed from the first light-blocking wall 42, and is helpful for heat dissipation from the light-receiver 41 and electrical connection with the external circuit.

Each of the first and second leg portions 23, 24 has an upper section 231 or 241, an extending section 232 or 242, and a terminal section 233 or 243. The upper sections 231, 241 extend from the respective second sides 212 of the support portion 21 in direction away from the first opening 40. The extending sections 232, 242 extend downwardly from the respective upper sections 231, 241. The terminal sections 233, 243 extend from the respective extending sections 232, 242 in directions away from the first opening 40. In addition, the terminal sections 233, 243 have bottom ends respectively formed with bonding surfaces 234, 244 for bonding with a PCB (not shown). The bonding surfaces 234, 244 are coplanar with the back face 214 (see FIG. 7).

Each of the third and fourth leg portions 32, 33 has a top section 321 or 331, a linking section 322 or 332, and a terminal section 323 or 333. The top sections 321, 331 are proximal to the respective second openings 50. The linking sections 322, 332 extend downwardly from the respective top sections 321, 331. The terminal sections 323, 333 extend from the respective linking sections 322, 332 in directions away from the respective second openings 50. In addition, the terminal sections 323, 333 have respective bonding surfaces 324, 334 to bond with the PCB. The bonding surfaces 324, 334 are coplanar with the back face 214 (see FIG. 7).

Referring back to FIGS. 2 to 4, the light-receiver 41 has a lead wire 412 electrically connecting the upper section 231 of the first leg portion 23, and establishes an electrical connection with the external circuit through the bonding surfaces 234, 244 of the first and second leg portions 23, 24. The light-emitter 51 of each of the light-emitting units 5 has two lead wires 512. The lead wires 512 are respectively and electronically connected to the top sections 321, 331 of the third and fourth leg portions 32, 33, thereby establishing an electrical connection with the external circuit through the bonding surfaces 324, 334 of the terminal sections 323, 333. As such, not only the light-receiver 41 and the light-emitters 51 are capable of independent electronic control, but a subsequent design of circuit layout for installing the optical sensor module (O) on a device can be simplified. In this embodiment, the lead wire 412 of the light-receiver 41 is electronically connected to the upper section 231 of the first leg portion 23 by wire bonding, which causes an increase in thickness of the optical sensor module (O). However, due to the downset configuration of the support portion 21, the height of the lead wire 412 can be lowered, thereby facilitating slimming of the optical sensor module (O).

Figure 7:
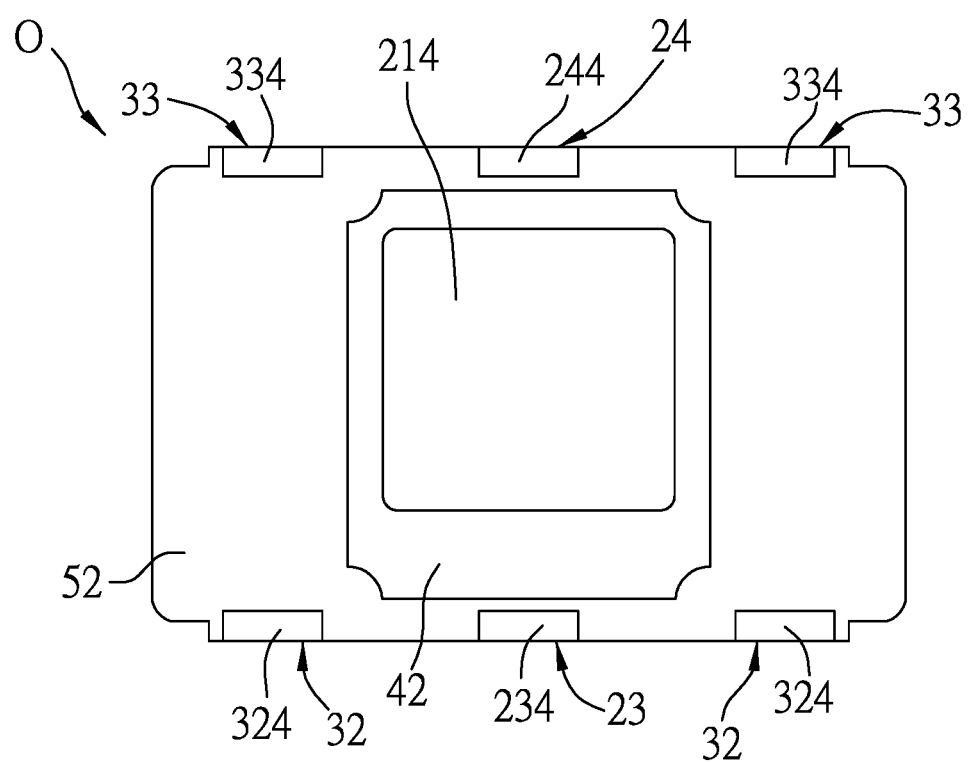
FIG. 7 is a bottom view of the optical sensor module of the first embodiment.

Referring back to FIGS. 4 and 6, for each of the projecting portions 22 of the main plate 2, the connection section 223 has two opposite ends that are respectively adjacent to the first and second leg portions 23, 24 and that are respectively formed with arcuate notched edges 225 indented toward the first opening 40. For each of the side plates 3, each of the third and forth leg portions 32, 33 has a concave edge 325 or 335 that is formed at a junction of the top section 321 or 331 and the linking section 322 or 332 and that is concaved in a direction away from the first opening 40. The concaved edges 325, 335 of the third and fourth leg portions 32, 33 face respectively the arcuate notched edges 225 of the projecting portions 22 of the main plate 2. As shown in FIG. 7, the second light-blocking wall 52 extends around the first light-blocking wall 42, and is molded over the first and second leg portions 23, 24 and the third and fourth leg portions 32, 33. In this embodiment, the bonding surfaces 234, 244 of the first and second leg portions 23, 24 and the bonding surfaces 324, 334 of the third and fourth leg portions 32, 33 are exposed from the bottom face of the light-blocking second wall 52.

Because the light-blocking second wall 52 only exposes the bonding surfaces 234, 244 of the first and second leg portions 23, 24 and the bonding surfaces 324, 334 of the third and fourth leg portions 32, 33, the terminal sections 233, 243, 323, 333 of the first, second, third and fourth leg portions 23, 24, 32, 33 are prevented from unwanted contact with an external object, which can affect the electrical connection among the light-receiver 41 and the light-emitters 51. Further, the back face 214 of the support portion 21 is exposed from to the first light-blocking wall 42, and is coplanar with the bottom faces of the first light-blocking wall 42 and the light-blocking second wall 52 so that an electrical connection with an external circuit can be established easily.

Referring back to FIGS. 2, 4 and 6, the first light-blocking wall 42 partially encloses the connection sections 223 of the projecting portions 22 and entirely encloses the arcuate notched edges 225. The arcuate notched edges 225 can increase the area of connection between the first light-blocking wall 42 and the main plate 2, so that the connection between the first light-blocking wall 42 and the main plate 2 can be effectively strengthened.

In this embodiment, the second light-blocking wall 52 extends around the first light-blocking wall 42 and is molded over the first and second leg portions 23, 24 and the third and fourth leg portions 32, 33. The connection sections 223 of the projecting portions 22 are partially enclosed by the second light-blocking wall 52. The concaved edges 325, 335 of the third and fourth leg portions 32, 33 enclosed by the first light-blocking wall 52 can increase the area of connection between the second light-blocking wall 52 and the side plates 3, so that the connection of the second light-blocking wall 52 and the side plates 3 can be effectively strengthened.

As shown in FIG. 2, the first light-blocking wall 42 has an outer surrounding surface 426 that surrounds the opening 40 and that has four arcuate grooves 427 indented toward the opening 40 from the outer surrounding surface 426 at positions respectively adjacent to the arcuate notched edges 225 of the main plate 2. The arcuate grooves 427 can increase the area of connection between the second light-blocking wall 52 and the first light-blocking wall 42, so that the connection of the second light-blocking wall 52 and the first light-blocking wall 42 can be effectively strengthened.

As shown in FIG. 4, the first light-blocking wall 42 further has an inner surrounding surface 422 surrounding the light-receiver 41 and defining the first opening 40. The inner surrounding surface 422 has a sloping surface section 423, a horizontal surface section 424 and an anti-overflow surface section 425. The sloping surface section 423 contacts and extends obliquely and upwardly from the support face 213. The horizontal surface section 424 extends horizontally from a top end of the sloping surface section 423 and away from the light receiver 41. The anti-overflow surface section 425 extends upwardly from the horizontal surface section 424 and away from the support face 213. The second light blocking wall 52 further has two inner surrounding surfaces 522 respectively defining the second openings 50. Each inner surrounding surface 522 has a sloping surface section 523, a horizontal surface section 524 and an anti-overflow surface section 525. The sloping surface section 523 contacts and extends obliquely and upwardly from the mounting face 311. The horizontal surface section 524 extends horizontally from the sloping surface section 523 and away from the light-emitter 51. The anti-overflow surface section 525 extends upwardly from the horizontal surface section 524 and away from the mounting face 311. In other words, each of the first and second light-blocking walls 42, 52 has a stepped configuration close to the open end of the first or second opening 40 or 50 due to presence of the horizontal surface section 424, or 524 and the anti-overflow surface section 425 or 525 connected to the sloping surface section 423 or 523. During the process of molding the first and second light-transmissible encapsulants 43, 53, the stepped configurations of the first and second light-blocking walls 42, 52 are able to avoid the materials of the first and second light-transmissible encapsulants 43, 53 from overflowing and transferring between the first and second openings 40, 50. As the problem of overflow may be avoided, crosstalk interference (i.e., signal interference) caused by the problem may be alleviated.

Referring back to FIG. 4, a first normal line (n1) is perpendicular to an edge of the light-receiving face 411. A first connection line (L1) extends from the edge of the light-receiving face 411 to the top end of the anti-overflow surface section 425. An included angle (θ1) between the first normal line (n1) and the first connection line (L1) ranging from 50 degrees to 70 degrees, for example, 60 degrees. Further, a second normal line (n2) is perpendicular to an edge of the light-emitting face 511. A second connection line (L2) extends from the edge of the light-emitting face 511 to the top end of the anti-overflow surface section 525. An included angle (θ2) between the second normal line (n2) and the second connection line (L2) ranging between 50 degrees and 70 degrees, for example, 60 degrees.

The first light-blocking wall 42 further has a top face 421 higher than a top face 521 of the second light-blocking wall 52. The higher top face 421 of the first light-blocking wall 42 prevents the light-receiver 41 from receiving the lights emitted directly from the light-emitters 51 and other stray lights. On the other hand, the first and second light blocking walls 42, 52 are made from one of a light-absorbing material and a light-reflecting material. To prevent the light-receiver 41 from receiving stray lights, the first light-blocking wall 42 may be made from a black opaque material. To increase the light-emitting effect of the light-emitters 51 and to enhance the SNR ratio of the optical sensor module (O), the second light-blocking wall 52 may be made from one of a black opaque material and a white opaque material.

Because the sloping surface section 523 of each inner surrounding surface 522 is used to reflect the light emitted from the respective light-emitter 51, an included angle between the sloping surface section 523 of the inner surrounding surface 522 and the mounting faces 311 of the respective side plate 3 is arranged to be an obtuse angle ranging from 115 degrees to 125 degrees. As such, the sloping surface section 523 of each inner surrounding surface 522 and the mounting face 311 of the respective side plate 3 may form a reflective cup shape, which can increase the light-emitting effect of the respective light-emitter 5. Similarly, the inner surrounding surface 422 of the first light-blocking wall 42 and the support face 213 of the main plate 2 may form a reflective cup shape to enhance the light-receiving effect of the light-receiver 41.

Figure 8:
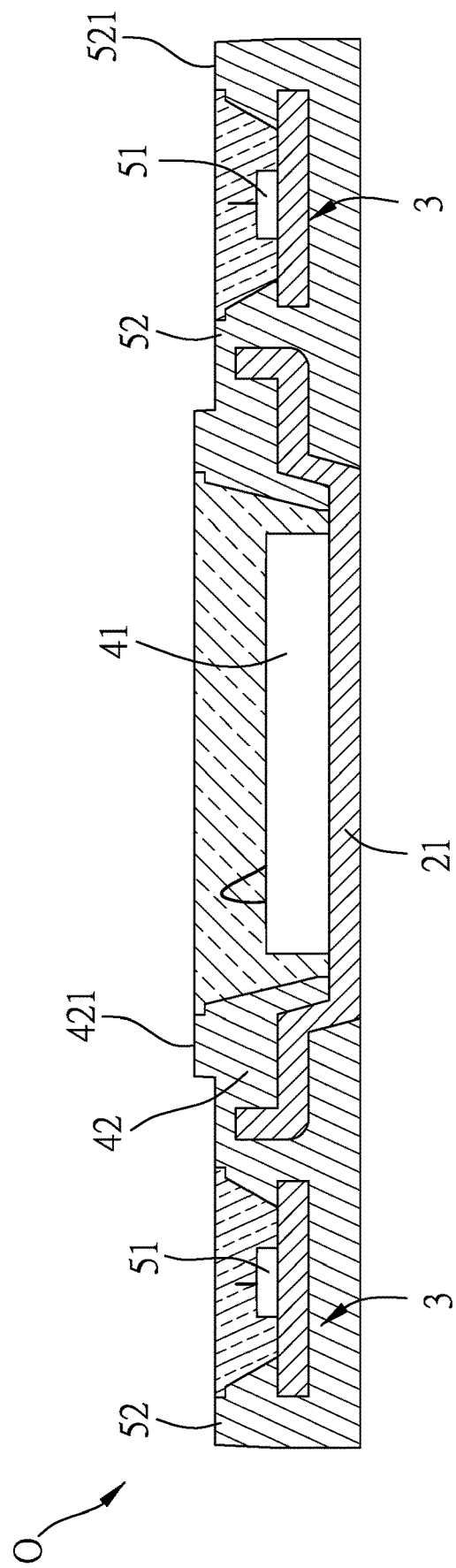
FIG. 8 is a sectioned view of an optical sensor module according to a second embodiment of the present disclosure.
Figure 9:
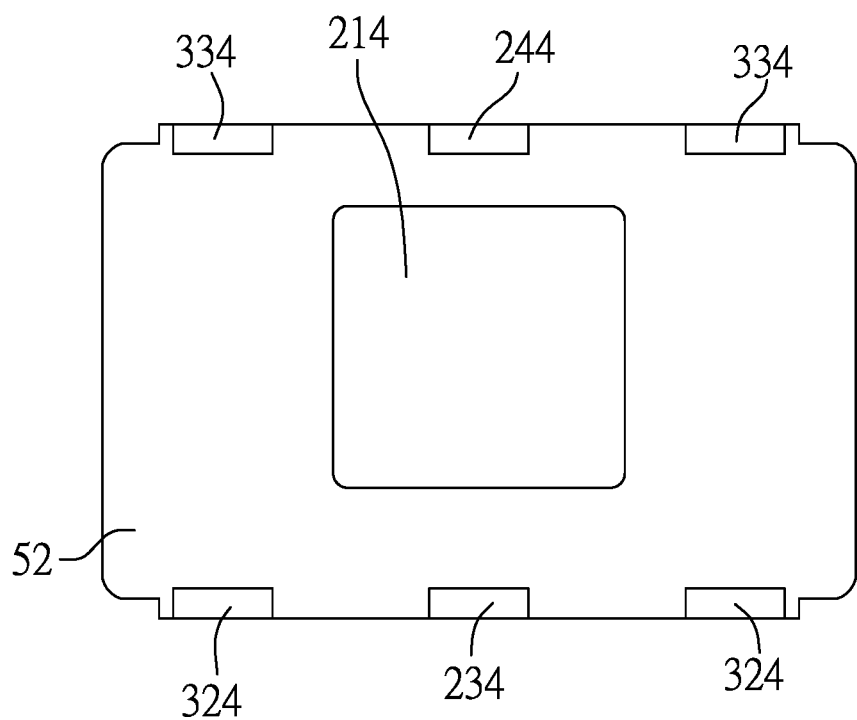
FIG. 9 is a bottom view of the optical sensor module of the second embodiment.

FIGS. 8 and 9 illustrate an optical sensor module (O) according to a second embodiment of the present disclosure, which is generally similar to the first embodiment. The differences of the second embodiment reside in that the housing over the lead frame (L) is molded as a one-piece unitary unit to enclose or embed the main plate 2 and the side plate 3. That is to say that the first and second light-blocking walls 42, 52 are made from the same material and formed integrally in a same molding process simultaneously. In addition, the first light-blocking wall 42 has a top face 421 higher than a top face 521 of said second light-blocking wall 52, preferably. Thus, the top face of the housing is a step structure, which the part of the top face surrounding the light-receiver 41 is higher than the part of the top face surrounding the light-emitter 51. In addition, the back face 214 of the main plate 2 and the bonding surfaces 234, 244, 324, 334 are exposed from the one-piece unitary unit at the same level.

Figure 10:
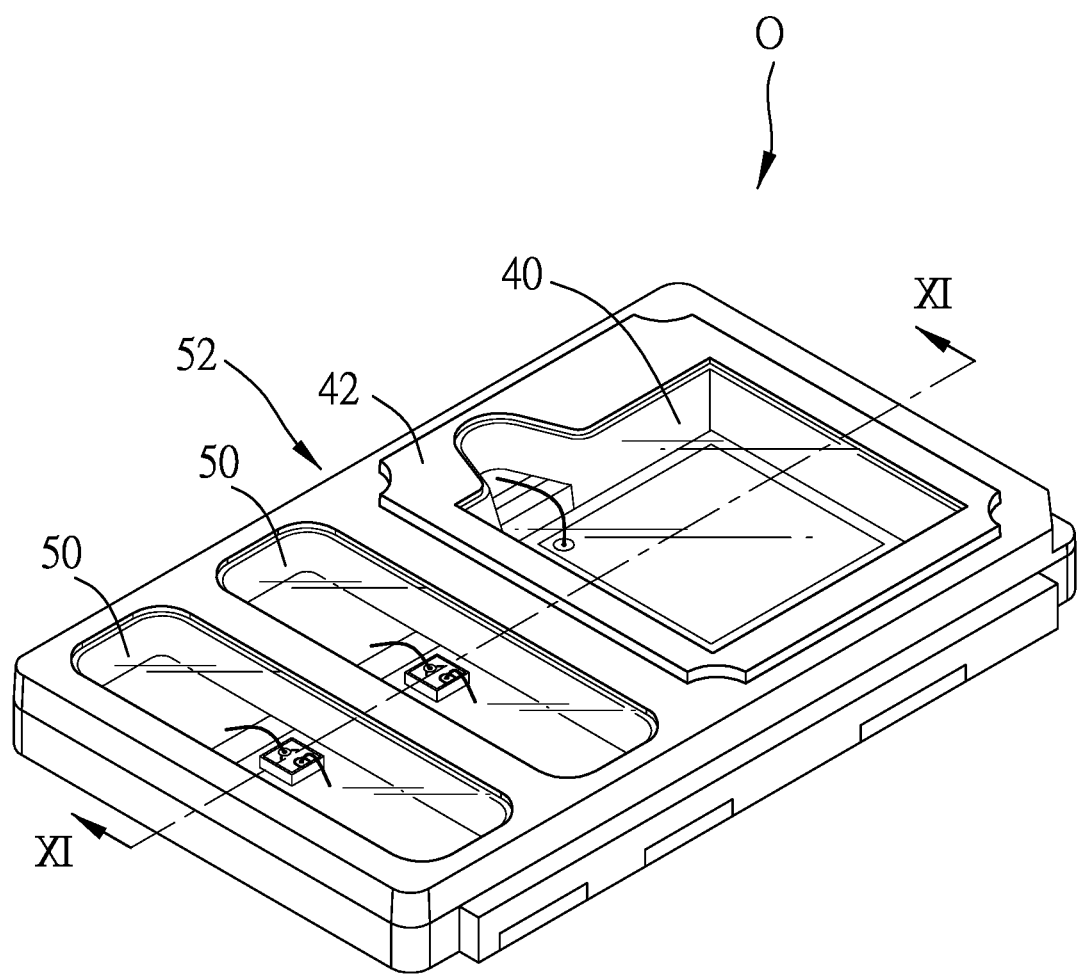
FIG. 10 is a perspective view of an optical sensor module according to a third embodiment of the present disclosure.
Figure 11:
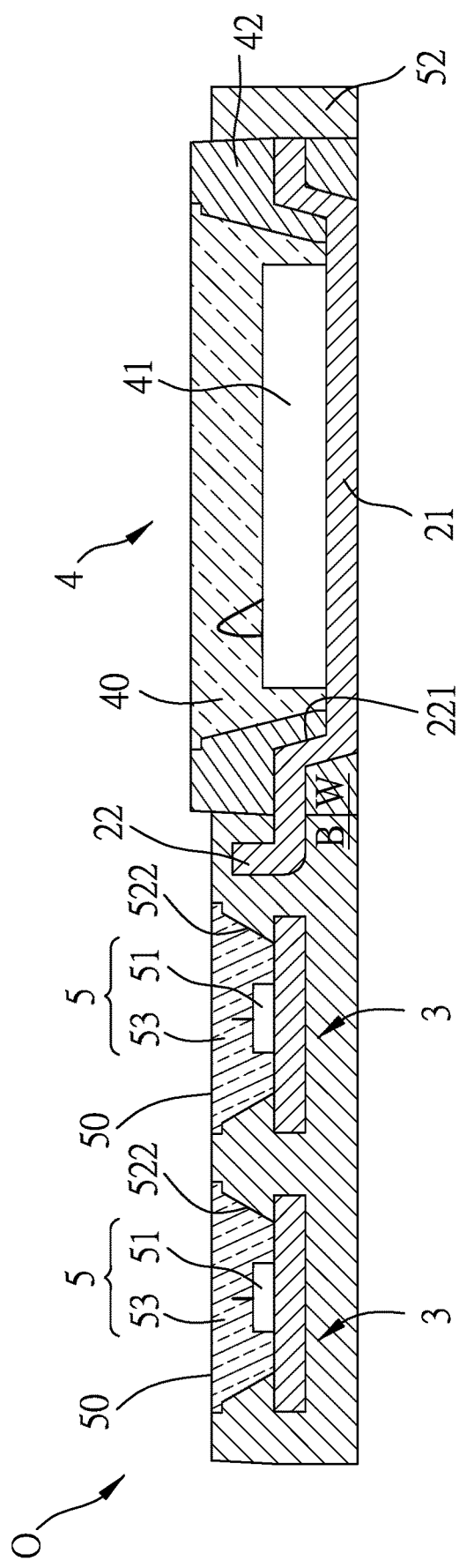
FIG. 11 is a section view taken along line XI-XI of FIG. 10.

FIGS. 10 and 11 illustrate an optical sensor module (O) according to a third embodiment of the present disclosure, which includes a lead frame (L), a receiver unit 4, a light-emitting unit 5 and a housing formed between the receiver unit 4 and the light-emitting unit 5, and which is generally similar to the first embodiment.

First, the lead frame (L) includes a main plate 2 and a side plate 3. The main plate 2 has a support portion 21 and a projecting portion 22. The support portion 21 has two opposite first sides 211 and a support face 213 located between the two opposite first sides 211. The projecting portion 22 projects upward from one of the two opposite first sides 211 in a direction opposite to the support face 213. The projecting portion 22 has a top face 221 extending away from the support face 213.

The side plate 3 is disposed separately from the one of the opposite first sides 211 of the support portion 21 and is spaced apart from the projecting portion 22.

The receiver unit 4 includes a light-receiver 41 that is disposed on the support face 213 and that has a light receiving face 411 opposite to the support face 213.

The light-emitting unit 5 includes a light-emitter 51 that is disposed on a mounting face 311 of the side plate 3 and that has a light-emitting face 511 opposite to the mounting face 311.

The housing is molded over the lead frame (L), and includes a first light blocking wall 42 and a second light-blocking wall 52. The first light blocking wall 42 has a first opening 40 exposing the light-receiver 41. The second light-blocking wall 52 has a second opening 50 exposing the light-emitting unit 5. The first and second light-blocking walls 42, 52 adjoin each other between the first and second openings 40, 50 to form a common light barrier wall.

The projecting portion 22 is at least partially enclosed by the common light barrier wall between the first opening 40 and the second opening 50, and the top face 221 of the projecting portion 22 is higher than the light receiving face 411 and the light-emitting face 511.

In addition, at least one side plate 3 further includes the two side plates 3 that are spaced apart from each other and are proximal to and spaced apart from one of the opposite first sides 211 of the support portion 21 of the main plate 2.

The second light-blocking wall 52 surrounds the first light-blocking wall 42, and has two second openings 50. Thus, the main plate 2 has only one projecting portion 22 disposed between the first opening 40 and one of the second openings 50, and is enclosed by the common light barrier wall. Therefore, one of the side plates 3 is interposed between the other one of the side plates 3 and the projecting portion 22.

Further, it should be noted that the number of each of the side plate 3, the light-emitting unit 5, the second opening 50 and the common light barrier wall is not limited to that required in the aforesaid embodiments, and may vary according to the requirements of practice application.

FIGS. 12 to 17 illustrate an example of a process for forming the optical sensor module 2 according to the first embodiment of the present disclosure.

Figure 12:
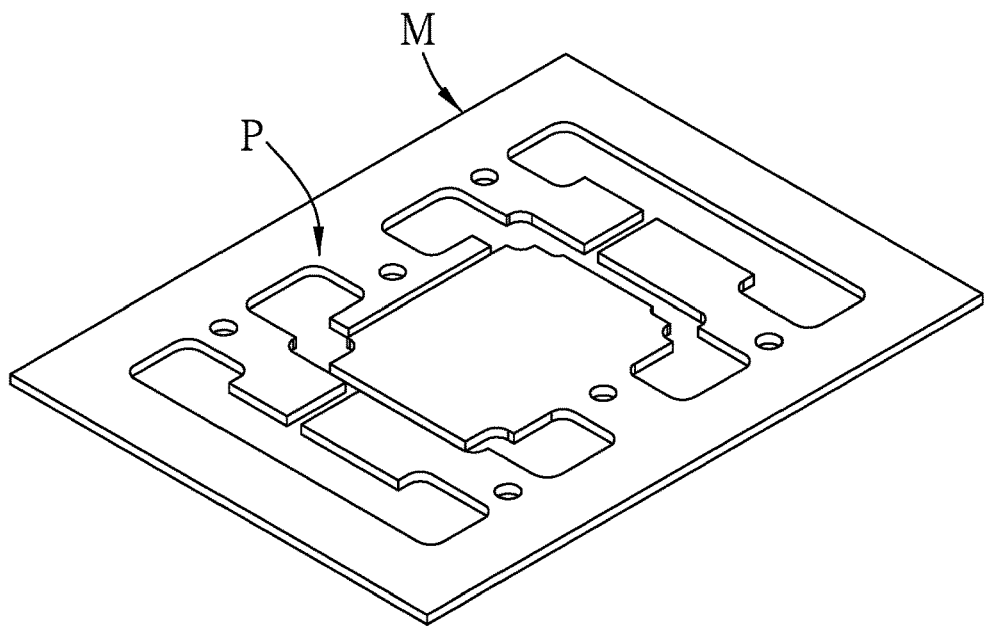
FIGS. 12 to 17 illustrate consecutive steps of an exemplified method of forming the optical sensor module of the first embodiment.

As shown in FIG. 12, a metal plate M, such as a copper plate, is cut and formed into a flat lead frame structure P by using a punching mold.

Figure 5:
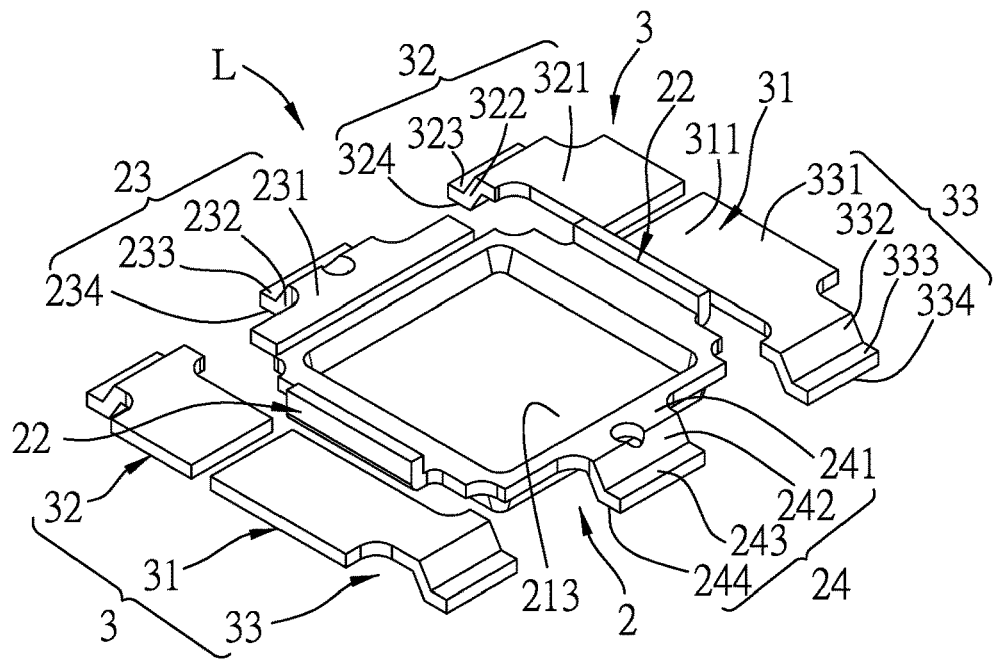
FIG. 5 is a perspective view, illustrating a lead frame of the first embodiment.
Figure 6:
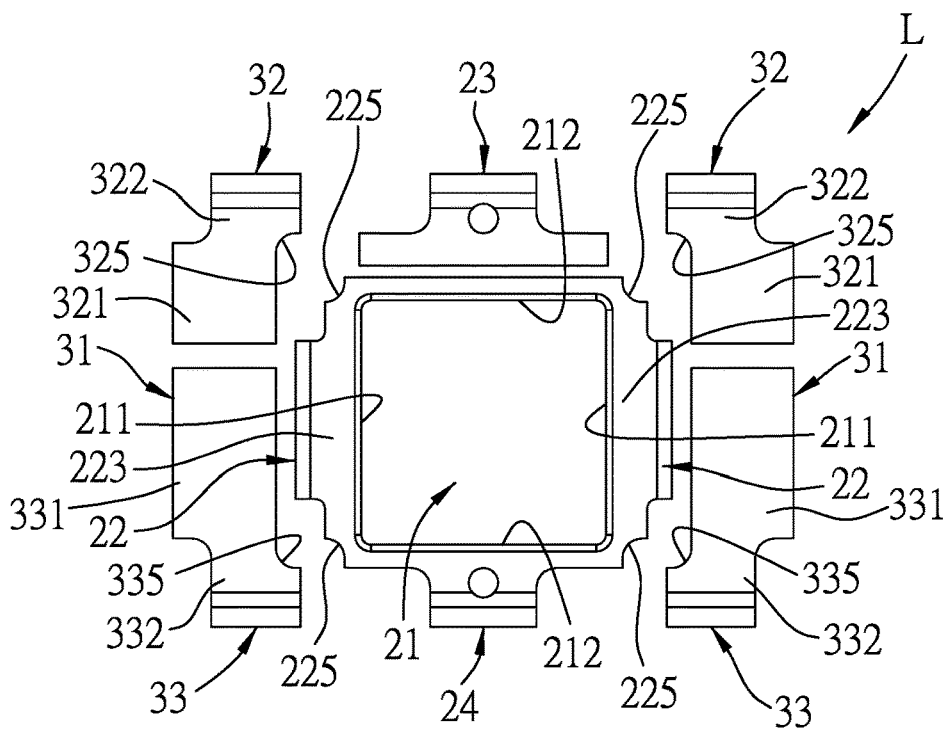
FIG. 6 is a top view of the lead frame of the first embodiment.
Figure 13:
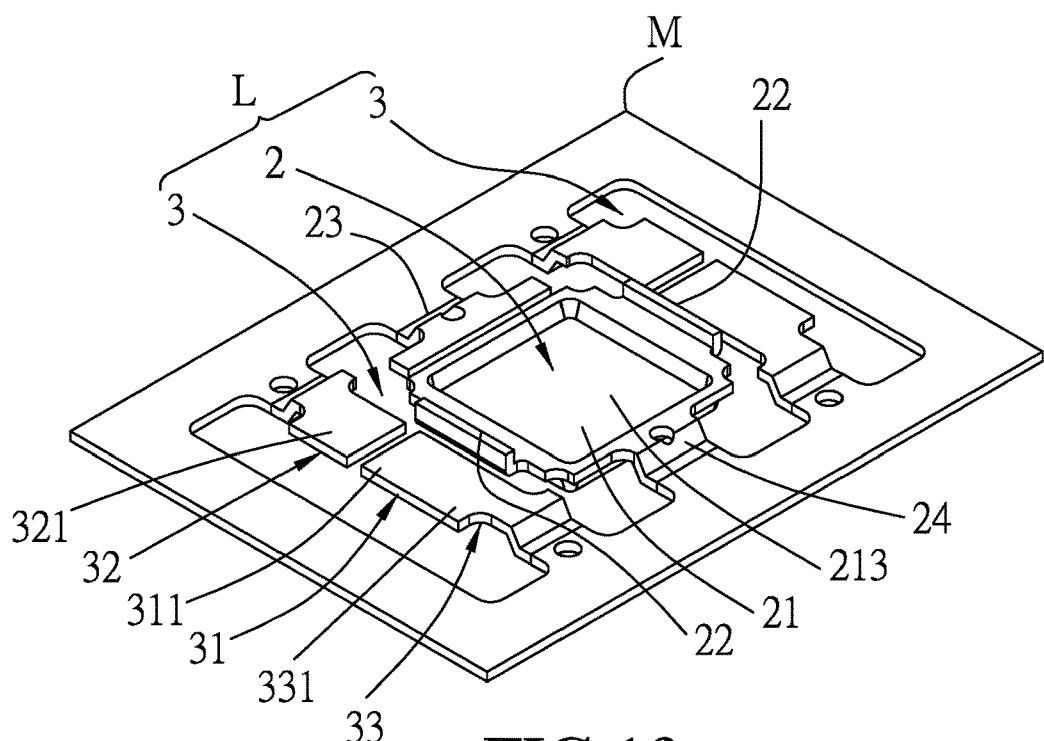

As shown in FIG. 13, in combination with FIG. 5, the flat lead frame structure P is punched and shaped to form the lead frame (L).

Figure 14:
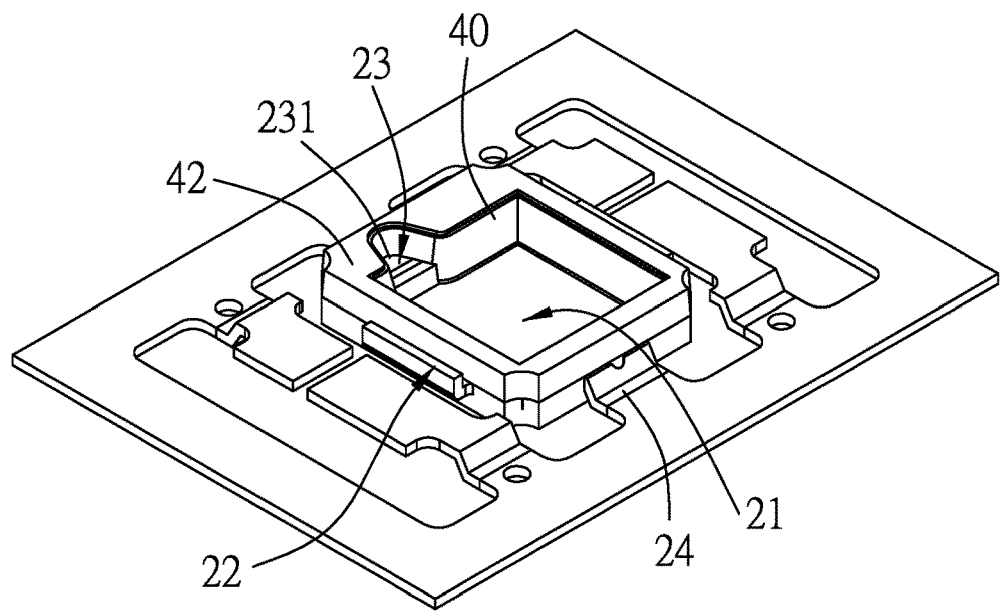
Figure 15:
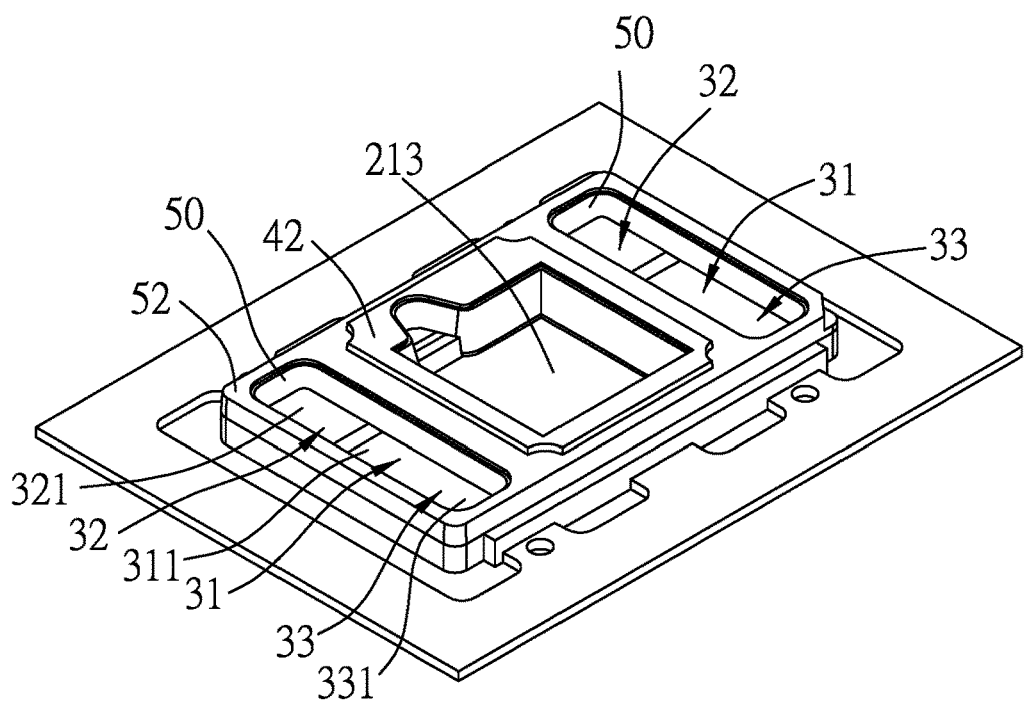

As shown in FIGS. 14 and 15, the first and second light-blocking walls 42 and 52 are formed consecutively through a two-step injection molding process. The first light-blocking wall 42 is molded over the main plate 2. The second light-blocking wall 52 is molded over the side plates 3 and extends around the first light-blocking wall 42.

Figure 16:
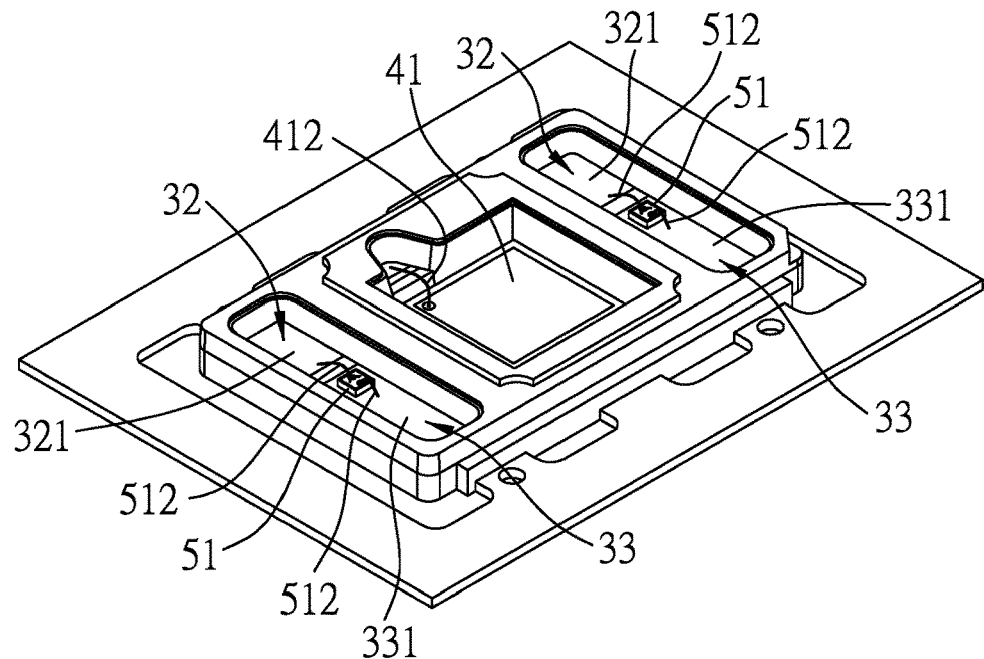

As shown in FIG. 16, the light-receiver 41 and the light-emitters 51 are respectively installed on the support face 213 of the main plate 2 and the mounting faces 311 of the side plates 3. The lead wire 412 is connected to the light receiver 41 and the upper section 231 of the first leg portion 23 by wire bonding. Each lead wire 512 is connected to one of the light emitters 51 and one of the top sections 321, 331 of the third and fourth leg portions 32, 33 of the respective side plate 3 by wire bonding.

Figure 17:
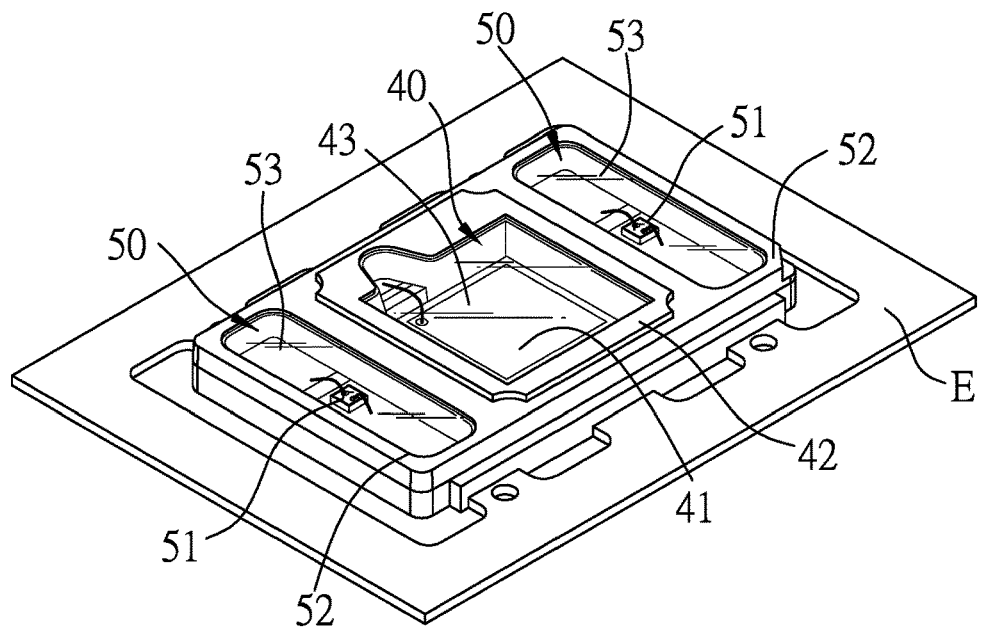

As shown in FIG. 17, the first light-transmissible encapsulant 43 is formed to fill the first opening 40 and encapsulates the light-receiver 41. Two second light-transmissible encapsulants 53 are formed to fill the respective second openings 50 and encapsulate the respective light-emitters 51.

Finally, the extra part (E) of the lead frame (L) that surrounds the second light-blocking wall 52 is cut off by punching to obtain the optical sensor module (O) (See FIG. 2).

While the first and second light-blocking walls 42, 52 are consecutively formed in the process as described hereinabove, the first and second light-blocking walls 42, 52 may be molded simultaneously through a one-step injection molding process according to the present enclosure.

Referring back to FIGS. 2 and 4, the optical sensor module (O) of the first embodiment may be connected to a printed circuit board (not shown) by soldering the bonding surfaces 234, 244 of the first and second leg portions 23, 24 and the bonding surfaces 324, 334 of the third and fourth leg portions 33, 34 to respective contact points on the printed circuit board. Because the support portion 21 of the main plate 2 is a downset and the back face 214 thereof is exposed from the first light-blocking wall 42, the back face 214 can be in direct contact with the surface of the printed circuit board, thereby enhancing heat dissipation of the light receiver 41 and avoiding signal deviation. In addition, each side plate 3 is made from metal so that heat from the light-emitters 51 may be effectively dissipated through the mounting faces 311 of the side plates 3. As shown in FIG. 5, because the third and fourth leg portions 32, 33 have a bent structure and respectively include the top sections 321, 331, the linking sections 322, 332 and the terminal sections 323, 333, when the optical sensor module (O) is mounted to the printed circuit board, the light emitting face 511 of the light-emitters 51 may be close to a target object (not shown), and the light receiver 41 may efficiently receive the light reflected from the target object.

Figure 18:
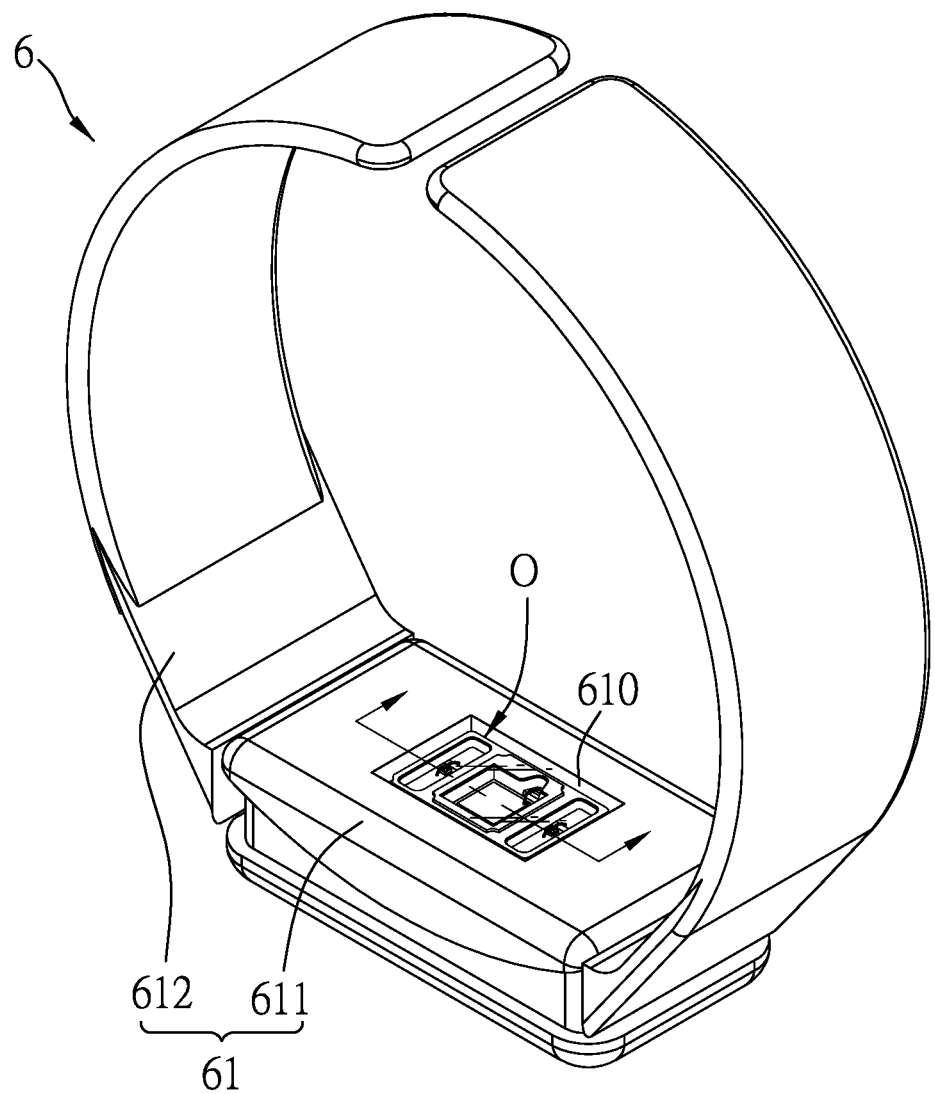
FIG. 18 illustrates a wearable device including the optical sensor module of the first embodiment.
Figure 19:
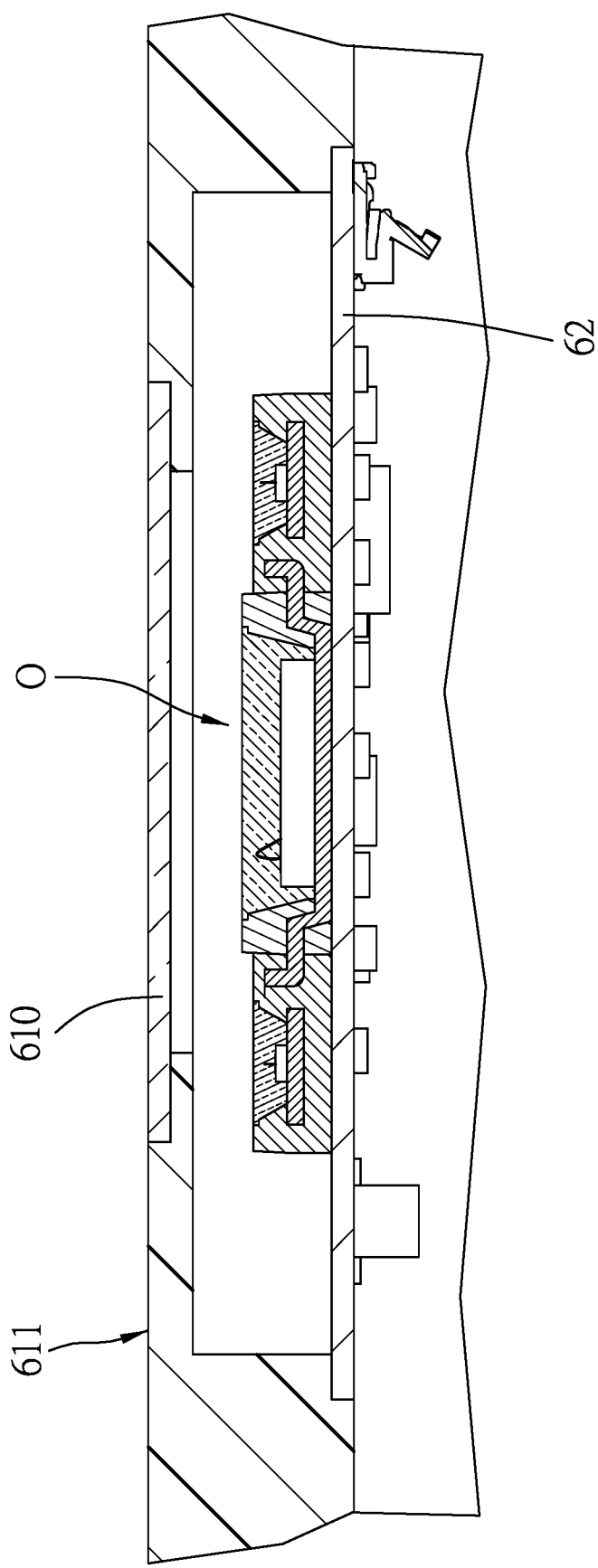
FIG. 19 is a fragmentary sectional view of FIG. 18.

FIGS. 18 and 19 illustrate a wearable device 6 according to the present disclosure, which is wearable by a user with skin contact to record photoplethysmogram (PPG) signals. The wearable device 6 includes a casing 61, a printed circuit board 62 and the optical sensor module (O) of the first embodiment.

The casing 61 includes a casing body 611 and a wearing member 612 connected to the casing body 611 to be worn by the user. The casing body 611 has a cover 610 for contacting the user's skin. The casing 61 is designed to be the form of a watch or a bracelet. The wearing member 612 is curved between two opposite ends of the casing body 611 and may be worn on the user's wrist. In addition, the cover 610 can be a transparent cover or a partially transparent cover, such that the cover 610 should be corresponding to predetermined light emitting paths and predetermined light receiving paths.

The printed circuit board 62 is disposed in the casing body 611 and parallel with the cover 610.

The optical sensor module (O) of the first embodiment is electrically connected to the printed circuit board 62 and located between the cover 610 and the printed circuit board 62. The first, second, third and fourth leg portions 23, 24, 32, 33 of the lead frame (L) (see FIGS. 5-7) are surface mounted to the printed circuit board 62.

As shown in FIGS. 4 and 18, when the wearable device 6 is worn by the user, the lights of the light-emitters 51 are emitted toward the user's skin and reflected by the user's skin to the light-receiver 41, so that the light-receiver 41 can produce PPG signals. Because the top face 421 of the first light-blocking wall 42 is higher than the top face 521 of the second light-blocking wall 52, and because the top faces 221 of the projecting portions 22 are higher than the light receiving face 411 of the light-receiver 41 and the light emitting faces 511 of the light-emitters 51, the lights of the light-emitters 51 may be prevented from entering directly the light-receiver 41, and the light-receiver 41 can assuredly receive the lights reflected by the user's skin.

Figure 20:
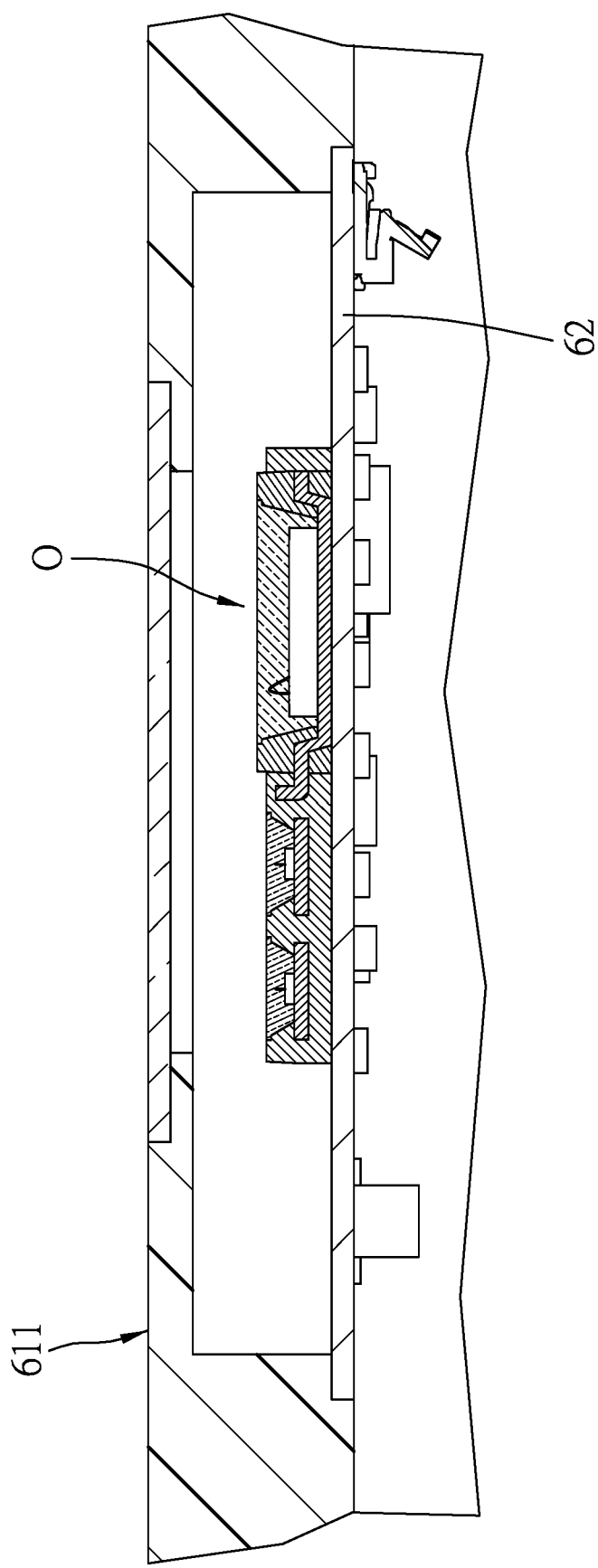
FIG. 20 is a fragmentary sectional view, illustrating the wearable device including the optical sensor module of the third embodiment.

FIG. 20 illustrates another wearable device 6 according to the present disclosure, which includes the optical sensor module (O) of the third embodiment.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A lead frame for an optical sensor module, comprising:
   a main plate having a support portion and at least one projecting portion, said support portion having two opposite first sides and a support face located between said two opposite first sides, said at least one projecting portion projecting upward from one of said two opposite first sides in a direction opposite to said support face; and
   at least one side plate that is disposed separately from said one of said two opposite first sides of said support portion and that is spaced apart from said at least one projecting portion.

2. The lead frame as claimed in claim 1, wherein top of said at least one projecting portion is higher than the top of the said support face of said support portion and the top of said side plate.

3. The lead frame as claimed in claim 1, wherein said at least one projecting portion has an inclined section, a connection section and a light partition section, said inclined section adjoining said one of said two opposite first sides and inclining said support face by an obtuse angle, said connection section extending horizontally from said inclined section toward a mounting face of said at least one side plate, said light partition section extending upwardly from said connection section in a direction away from said support face.

4. The lead frame as claimed in claim 1, wherein:
said main plate further has a first leg portion and a second leg portion, said first leg portion being spaced apart from said support portion, said second leg portion being connected to said support portion; and
said at least one side plate has a mount portion, a third leg portion and a fourth leg portion, said mount portion having a mounting face, said third leg portion being spaced apart from said mount portion, said fourth leg portion being connected to said mount portion.

5. The lead frame as claimed in claim 4, wherein said third leg portion is disposed at the same side as that of said first leg portion, and said fourth leg portion is disposed at the same side as that of said second leg portion.

6. The lead frame as claimed in claim 4, wherein:
each of said first and second leg portions has
an upper section extending from one of said two opposite second sides,
an extending section extending downwardly from said upper section, and
a terminal section extending from said extending section for making an electrical connection with an external circuit; and
each of said third and fourth leg portions has
a top section,
a linking section extending downwardly from said top section, and
a terminal section extending from said linking section for making an electrical connection with an external circuit.

7. The lead frame as claimed in claim 4, wherein said at least one projecting portion further has two opposite ends that are respectively adjacent to said first and second leg portions and that are respectively formed with arcuate notched edges, each of said third and fourth leg portions further has a concaved edge, said concaved edges of said third and fourth leg portions facing respectively said arcuate notched edges of said at least one projecting portion of said main plate.

8. The lead frame as claimed in claim 1, wherein said at least one side plate includes two side plates that are respectively proximal to and spaced apart from said two opposite first sides of said support portion, and said at least one projecting portion includes two projecting portions, which respectively project from said two opposite first sides of said support portion.

9. The lead frame as claimed in claim 1, wherein said at least one side plate includes two side plates that are spaced apart from each other and that are proximal to and spaced apart from one of said two opposite first sides of said supporting portion.

10. An optical sensor module comprising:
a lead frame as claimed in claim 1;
a receiver unit including
a light receiver that is disposed on said support face and that has a light receiving face opposite to said support face;
at least one light-emitting unit including
a light-emitter that is disposed on a mounting face of said at least one side plate and that has a light-emitting face opposite to said mounting face; and
a housing molded over said lead frame.

11. The optical sensor module as claimed in claim 10, wherein said housing comprises:
a first light-blocking wall that has a first opening exposing said light-receiver; and
a second light-blocking wall that has at least one second opening exposing said light-emitting unit, wherein said first and second light-blocking walls adjoin each other between said first and second openings to form at least one common light barrier wall.

12. The optical sensor module as claimed in claim 10, wherein said at least one projecting portion has an inclined section, a connection section and a light partition section, said inclined section adjoining said one of said two opposite first sides and inclining said support face by an obtuse angle, said connection section extending horizontally from said inclined section toward said mounting face of said at least one side plate, said light partition section extending upwardly from said connection section in a direction away from said support face.

13. The optical sensor module as claimed in claim 11, wherein said first light-blocking wall has an outer surrounding surface that surrounds said opening and that has two arcuate grooves indented toward said opening from said outer surrounding surface at positions respectively adjacent to said arcuate notched edges of said main plate.

14. The optical sensor module as claimed in claim 11, wherein said first light-blocking wall further has an inner surrounding surface defining said first opening, said inner surrounding surface of said first light-blocking wall having a sloping surface section contacting and extending obliquely and upwardly from said support face, a horizontal surface section extending horizontally from a top end of said sloping surface section and away from said light receiver.

15. The optical sensor module as claimed in claim 11, wherein said second light blocking wall further has an inner surrounding surface defining said at least one second opening, said inner surrounding surface of said second light blocking wall having a sloping surface section contacting and extending obliquely and upwardly from said mounting face, a horizontal surface section extending horizontally from said sloping surface section and away from said light-emitter.

16. The optical sensor module as claimed in claim 10, wherein said receiver unit further includes a first light-transmissible encapsulant encapsulating said light receiver and covering said support face, and said at least one light-emitting unit further includes a second light-transmissible encapsulant encapsulating said light-emitter and covering said mounting face.

17. The optical sensor module as claimed in claim 11, wherein said first light-blocking wall is made from a first black opaque material, and said second light-blocking wall is made from one of a second black opaque material and a white opaque material.

18. The optical sensor module as claimed in claim 11, wherein said first light-blocking wall further has a top face higher than a top face of said second light-blocking wall.

19. A wearable device for being worn by a user with skin contact to record photoplethysmogram signals, said wearable device comprising:

a casing including a casing body and a wearing member connected to said casing body to be worn by a user, said casing body having a cover for contacting the user's skin;
a printed circuit board disposed in said casing body; and
an optical sensor module as claimed in claim 10 electrically connected to said printed circuit board and located between said cover and said printed circuit board.

20. The wearable device as claimed in claim 19, wherein said housing of said optical sensor module further comprises:
a first light-blocking wall that has a first opening exposing said light-receiver; and
a second light-blocking wall that has at least one second opening exposing said light-emitting unit, wherein said first light-blocking wall has a top face higher than a top face of said second light-blocking wall.

\* \* \* \* \*